United States Patent [19]

Bruemmer

[11] Patent Number: 5,685,873
[45] Date of Patent: Nov. 11, 1997

[54] DISPOSABLE DIAPER HAVING DIFFERENTIALLY STRETCHABLE EARS WITH CHILDPROOF FASTENING

[75] Inventor: Mary A. Bruemmer, Neenah, Wis.

[73] Assignee: Kimberly-Clark Worldwide, Inc., Neenah, Wis.

[21] Appl. No.: 220,405

[22] Filed: Mar. 30, 1994

Related U.S. Application Data

[63] Continuation of Ser. No. 757,788, Sep. 11, 1991, abandoned.
[51] Int. Cl.$^6$ ............................... A61F 13/15; A61F 13/20
[52] U.S. Cl. .................. 604/385.2; 604/373; 604/389; 604/391; 604/392
[58] Field of Search ............................... 24/304; 604/358, 604/367, 373, 385.1, 385.2, 386, 389–392

[56] References Cited

U.S. PATENT DOCUMENTS

| | | |
|---|---|---|
| 219,820 | 9/1879 | Kohl . |
| 584,490 | 6/1897 | Warren . |
| 879,774 | 2/1908 | Jonata . |
| 1,079,479 | 11/1913 | Earnshaw . |
| 1,096,477 | 5/1914 | Weisert . |
| 1,122,988 | 12/1914 | Myers . |
| 1,163,793 | 12/1915 | Taylor . |
| 1,188,223 | 6/1916 | Uyeda . |
| 1,195,904 | 8/1916 | Bornstein . |
| 1,288,848 | 12/1918 | Dudley . |
| 1,431,315 | 10/1922 | Le Moine . |
| 1,676,144 | 7/1928 | Houseknecht . |
| 1,740,973 | 12/1929 | Dietz . |
| 2,025,843 | 12/1935 | Anderson . |
| 2,292,030 | 8/1942 | Kraft . |
| 2,349,426 | 5/1944 | Harwood . |
| 2,492,265 | 12/1949 | Bryan . |
| 2,500,432 | 1/1950 | Ravkind et al. . |
| 2,508,811 | 5/1950 | Best et al. . |

(List continued on next page.)

FOREIGN PATENT DOCUMENTS

| | | |
|---|---|---|
| 132006 | 4/1990 | China . |
| 0013463A1 | 7/1980 | European Pat. Off. . |
| 0070163 | 1/1983 | European Pat. Off. . |
| 0070164 | 1/1983 | European Pat. Off. . |
| 0108637 | 5/1984 | European Pat. Off. . |
| 0174775 | 3/1986 | European Pat. Off. . |
| 0274753A2 | 7/1988 | European Pat. Off. . |
| 0317058A1 | 5/1989 | European Pat. Off. . |
| 0320991A2 | 6/1989 | European Pat. Off. . |
| 0377212A2 | 7/1990 | European Pat. Off. . |
| 0396050A2 | 11/1990 | European Pat. Off. . |
| 0403832A1 | 12/1990 | European Pat. Off. . |
| 0421473A2 | 4/1991 | European Pat. Off. . |
| 2585217 | 1/1987 | France . |
| 2586558 | 3/1987 | France . |
| 1491234 | 4/1969 | Germany . |
| 61-2854 | 1/1986 | Japan . |
| 63-123607 | 2/1987 | Japan . |
| 63-170406 | 11/1988 | Japan . |
| 3-7815 | 6/1989 | Japan . |
| 3-7815 | 1/1991 | Japan . |
| 2209672 | 5/1989 | United Kingdom . |
| 2214057 | 8/1989 | United Kingdom . |
| 2236663 | 4/1991 | United Kingdom . |
| WO 84/04242 | 11/1984 | WIPO . |
| WO86/05661 | 9/1985 | WIPO . |

OTHER PUBLICATIONS

U.S. application Serial No. 08/099,108, filed Jul. 28, 1993 in the name of M. A. Bruemmer which is a continuation–in–part of U.S. Application Serial No. 07/742/776 filed Aug. 8, 1991.

*Primary Examiner*—P. Zuttarelli
*Attorney, Agent, or Firm*—Jeffrey B. Curtin

[57] ABSTRACT

A disposable absorbent garment for use as a baby diaper and the like includes a pair of differentially stretchable ear members wherein each differentially stretchable ear member comprises a stretchable inner ear portion and a stretchable outer ear portion. A first fastening mechanism on each ear is releasably fastenable to the front of the article, and second fastenable members on the outermost portions of each stretchable ear are fastenable together at the front of the diaper when worn.

58 Claims, 3 Drawing Sheets

U.S. PATENT DOCUMENTS

| | | | |
|---|---|---|---|
| 2,509,674 | 5/1950 | Cohen . | |
| 2,516,951 | 8/1950 | Brink . | |
| 2,545,761 | 3/1951 | Brink . | |
| 2,564,094 | 8/1951 | Brandl . | |
| 2,566,139 | 8/1951 | Ostrovsky et al. . | |
| 2,575,054 | 11/1951 | Gowdy . | |
| 2,638,899 | 5/1953 | Ambarian . | |
| 2,675,805 | 4/1954 | Trimble . | |
| 2,701,567 | 2/1955 | Smith . | |
| 2,830,589 | 4/1958 | Doner . | |
| 2,853,073 | 9/1958 | Brafman . | |
| 2,910,982 | 11/1959 | Woodward . | |
| 2,926,666 | 10/1960 | Casper . | |
| 3,016,599 | 1/1962 | Perry . | |
| 3,050,063 | 8/1962 | Margraf . | |
| 3,162,196 | 12/1964 | Salk . | |
| 3,322,122 | 5/1967 | Daniel . | |
| 3,400,718 | 9/1968 | Saijo . | |
| 3,441,024 | 4/1969 | Ralph . | |
| 3,523,536 | 8/1970 | Ruffo . | |
| 3,530,859 | 9/1970 | Heimowitz . | |
| 3,572,342 | 3/1971 | Lindquist et al. . | |
| 3,595,235 | 7/1971 | Jespersen . | |
| 3,612,055 | 10/1971 | Mesek et al . | |
| 3,618,608 | 11/1971 | Brink . | |
| 3,663,348 | 5/1972 | Liloia et al. . | |
| 3,665,921 | 5/1972 | Stumpf . | |
| 3,730,184 | 5/1973 | Mesek . | |
| 3,745,587 | 7/1973 | Bradley . | |
| 3,768,480 | 10/1973 | Mesek et al. . | |
| 3,771,524 | 11/1973 | Ralph . | |
| 3,777,758 | 12/1973 | Mesek . | |
| 3,779,246 | 12/1973 | Mesek et al. . | |
| 3,800,796 | 4/1974 | Jacob . | |
| 3,825,006 | 7/1974 | Ralph . | |
| 3,837,343 | 9/1974 | Mesek . | |
| 3,931,666 | 1/1976 | Karami | 604/389 |
| 3,987,792 | 10/1976 | Hernandez et al. . | |
| 4,051,853 | 10/1977 | Egan, Jr. | 604/390 |
| 4,051,854 | 10/1977 | Aaron . | |
| 4,074,716 | 2/1978 | Schaar | 604/390 |
| 4,077,410 | 3/1978 | Butterworth et al. . | |
| 4,118,531 | 10/1978 | Hauser . | |
| 4,216,772 | 8/1980 | Tsuchiya et al. . | |
| 4,230,113 | 10/1980 | Mehta . | |
| 4,304,234 | 12/1981 | Hartmann . | |
| 4,333,782 | 6/1982 | Pieniak | 604/385.2 |
| 4,338,371 | 7/1982 | Dawn et al. . | |
| 4,342,808 | 8/1982 | Langen et al. . | |
| 4,352,355 | 10/1982 | Mesek et al. . | |
| 4,372,312 | 2/1983 | Fendler et al. . | |
| 4,374,888 | 2/1983 | Bornslaeger . | |
| 4,388,075 | 6/1983 | Mesek et al. . | |
| 4,397,645 | 8/1983 | Buell . | |
| 4,413,032 | 11/1983 | Hartmann et al. . | |
| 4,421,813 | 12/1983 | Athey . | |
| 4,430,086 | 2/1984 | Repke . | |
| 4,468,428 | 8/1984 | Early et al. . | |
| 4,475,912 | 10/1984 | Coates . | |
| 4,500,384 | 2/1985 | Tomioka et al. . | |
| 4,522,874 | 6/1985 | Pommez . | |
| 4,552,603 | 11/1985 | Harris, Jr. et al. . | |
| 4,568,344 | 2/1986 | Suzuki et al. | 604/390 |
| 4,573,987 | 3/1986 | Lamb, Jr. . | |
| 4,573,988 | 3/1986 | Pieniak et al. . | |
| 4,578,414 | 3/1986 | Sawyer et al. . | |
| 4,589,878 | 5/1986 | Mitrani . | |
| 4,610,682 | 9/1986 | Kopp . | |
| 4,617,022 | 10/1986 | Pigneul et al. . | |
| 4,626,305 | 12/1986 | Suzuki et al. . | |
| 4,639,949 | 2/1987 | Ales et al. . | |
| 4,642,819 | 2/1987 | Ales et al. . | |
| 4,643,729 | 2/1987 | Laplanche | 604/390 |
| 4,646,362 | 3/1987 | Heran et al. . | |
| 4,661,102 | 4/1987 | Shikata et al. . | |
| 4,675,015 | 6/1987 | Brown . | |
| 4,675,918 | 6/1987 | O'Brien . | |
| 4,681,581 | 7/1987 | Coates . | |
| 4,687,477 | 8/1987 | Suzuki et al. . | |
| 4,695,278 | 9/1987 | Lawson | 604/385.2 |
| 4,704,112 | 11/1987 | Suzuki et al. . | |
| 4,704,116 | 11/1987 | Enloe . | |
| 4,714,647 | 12/1987 | Shipp, Jr. et al. . | |
| 4,728,326 | 3/1988 | Gilles . | |
| 4,732,809 | 3/1988 | Harris, Jr. et al. . | |
| 4,738,677 | 4/1988 | Foreman . | |
| 4,743,246 | 5/1988 | Lawson . | |
| 4,773,906 | 9/1988 | Krushel . | |
| 4,795,452 | 1/1989 | Blaney et al. . | |
| 4,795,454 | 1/1989 | Dragoo . | |
| 4,798,603 | 1/1989 | Meyer et al. . | |
| 4,816,026 | 3/1989 | Richardson | 604/385.2 |
| 4,822,435 | 4/1989 | Igaue et al. . | |
| 4,826,499 | 5/1989 | Ahr . | |
| 4,830,904 | 5/1989 | Gessner et al. . | |
| 4,834,736 | 5/1989 | Boland et al. . | |
| 4,834,738 | 5/1989 | Kielpikowski et al. . | |
| 4,834,740 | 5/1989 | Suzuki et al. . | |
| 4,834,742 | 5/1989 | Wilson et al. . | |
| 4,842,596 | 6/1989 | Kielpikowski et al. . | |
| 4,846,823 | 7/1989 | Enloe . | |
| 4,846,825 | 7/1989 | Enloe et al. . | |
| 4,850,988 | 7/1989 | Aledo et al. . | |
| 4,850,992 | 7/1989 | Amaral et al. . | |
| 4,857,067 | 8/1989 | Wood et al. . | |
| 4,861,652 | 8/1989 | Lippert et al. . | |
| 4,874,666 | 10/1989 | Kubo et al. | 428/397 |
| 4,880,420 | 11/1989 | Pomparelli . | |
| 4,883,480 | 11/1989 | Huffman et al. . | |
| 4,883,481 | 11/1989 | Blanchard . | |
| 4,883,707 | 11/1989 | Newkirk | 604/372 |
| 4,892,528 | 1/1990 | Suzuki et al. . | |
| 4,895,568 | 1/1990 | Enloe . | |
| 4,895,569 | 1/1990 | Wilson et al. . | |
| 4,904,251 | 2/1990 | Igaue et al. . | |
| 4,909,803 | 3/1990 | Aziz et al. . | |
| 4,911,702 | 3/1990 | O'Leary et al. . | |
| 4,916,005 | 4/1990 | Lippert et al. . | |
| 4,917,696 | 4/1990 | De Jonckheere . | |
| 4,923,454 | 5/1990 | Seymour et al. . | |
| 4,936,840 | 6/1990 | Proxmire . | |
| 4,937,887 | 7/1990 | Schreiner . | |
| 4,938,753 | 7/1990 | Van Gompel et al. . | |
| 4,938,754 | 7/1990 | Mesek . | |
| 4,938,757 | 7/1990 | Van Gompel et al. . | |
| 4,940,464 | 7/1990 | Van Gompel et al. . | |
| 4,964,860 | 10/1990 | Gipson et al. . | |
| 4,973,326 | 11/1990 | Wood et al. . | |
| 4,978,570 | 12/1990 | Heyn et al. . | |
| 4,981,480 | 1/1991 | Gaudet et al. . | |
| 4,988,344 | 1/1991 | Reising et al. . | |
| 4,988,346 | 1/1991 | Pfefferkorn . | |
| 4,988,560 | 1/1991 | Meyer et al. . | |
| 4,994,054 | 2/1991 | Pigneul et al. . | |
| 5,019,073 | 5/1991 | Roessler et al. . | |
| 5,087,255 | 2/1992 | Sims . | |
| 5,137,526 | 8/1992 | Coates . | |
| 5,232,777 | 8/1993 | Sipinen et al. | 604/390 |
| B1 3,860,003 | 4/1989 | Buell . | |
| B1 4,636,207 | 11/1989 | Buell . | |

DISPOSABLE DIAPER HAVING DIFFERENTIALLY STRETCHABLE EARS WITH CHILDPROOF FASTENING

This is a continuation of application Ser. No. 07/757,788 filed on Sep. 11, 1991 now abandoned.

BACKGROUND OF THE INVENTION

This invention pertains to a disposable article, and more particularly to a disposable absorbent article having stretchable ears and childproof fastening for use in absorbing and containing body wastes.

Currently, disposable absorbent articles find widespread use in infant, child, and adult incontinence care, and have generally replaced reusable cloth absorbent articles. A typical disposable absorbent article generally comprises a composite structure including a topsheet, a backsheet, and an absorbent between the topsheet and backsheet. Generally, these absorbent articles also include some type of fastening system for fitting onto a wearer. Examples of such articles include baby diapers and adult incontinence garments.

Although current diapers or other absorbent articles have been generally accepted by the public, these articles still have need of improvement in certain areas. Specifically, mothers have indicated a desire for a baby diaper that cannot be unfastened by the baby. Generally, babies between the age of about 18 months to about 36 months begin to show a curiosity with their diaper that eventually leads to their playing with the conventional adhesive tapes that secure the diaper to the baby. In this age range, the babies have the dexterity and strength to unfasten the adhesive tapes and thus may remove the diaper at an inopportune time.

Although pant-like articles, which have a waist and a pair of leg openings, offer one type of solution to babies removing their diapers, these pant-like articles also require removal of outer clothing in order to pull the pant up or down the baby's legs.

SUMMARY OF THE INVENTION

In one form of the invention, there is provided an absorbent article comprising a front section, a back section, and a crotch section; and an absorbent medium positioned on at least the crotch section. A pair of stretchable ears are disposed on respective opposite side portions of the back section. Each stretchable ear includes a stretchable inner portion and a stretchable outer portion.

BRIEF DESCRIPTION OF THE DRAWINGS

The above-mentioned and other features of the present invention, and the manner of obtaining them, will become more apparent and the invention itself will be better understood by reference to the following description of the invention taken in conjunction with the accompanying drawings, wherein.

DESCRIPTION OF A PREFERRED EMBODIMENT

Within the context of the present disclosure, each term below will include the following meaning:

(a) "Disposed", "disposed on", "disposed with", "disposed at", "disposed near", and variations thereof, are intended to mean that one element can be integral with another element, or that one element can be a separate structure joined to or connected to or placed with or placed near another element.

(b) "Non-gathered" describes the effect of the stretchable leg cuffs of the present invention on the material or structure on which they are disposed, and is in contrast to the effect of leg elastics that are applied in the conventionally stretched condition to a diaper structure. In a conventional diaper, upon relaxing the stretched, attached leg elastics, they gather or shirr the diaper structure to which they are attached. In the present invention, the stretchable leg cuffs are attached so that they do not gather in a manner similar to leg elastics in a conventional diaper.

(c) "Stretch-bonded laminate" (SBL) means at least a two-layered composite in which one layer is a gatherable layer and the other layer a stretchable layer. The layers are joined together when the stretchable layer is in a stretched condition so that upon relaxing the layers, the gatherable layer is gathered and the stretchable layer is relaxed, non-gathered.

(d) "Snap action" has the meaning described in American Society for Testing and Material 4846-88, which is the force required to disengage a snap fastener resulting from a pull exerted perpendicular to the plane of material to which the snap fastener is attached.

These definitions are not intended to be limiting, and these terms may be defined with additional language in the remaining portion of the specification.

The diaper of the present invention includes a versatile fastening system that provides a more convenient diaper change, especially with older babies. The diaper can be fitted in the normal manner, which is while the baby is lying on his or her back. In addition, because the diaper of the present invention has stretchable ears with a snap-type closure for the ears, the diaper can be pulled up and down like a pair of training pants. The snap-type closure keeps the stretchable ears securely fastened together while the diaper is being pulled up and down, and also acts as a child-proof feature to prevent the baby from removing the diaper at inappropriate times. The diaper of the present invention is designed primarily to fit a baby that is approximately 18 months to 36 months old, and that weighs between about 22 to about 35 lbs.

Figure 3:
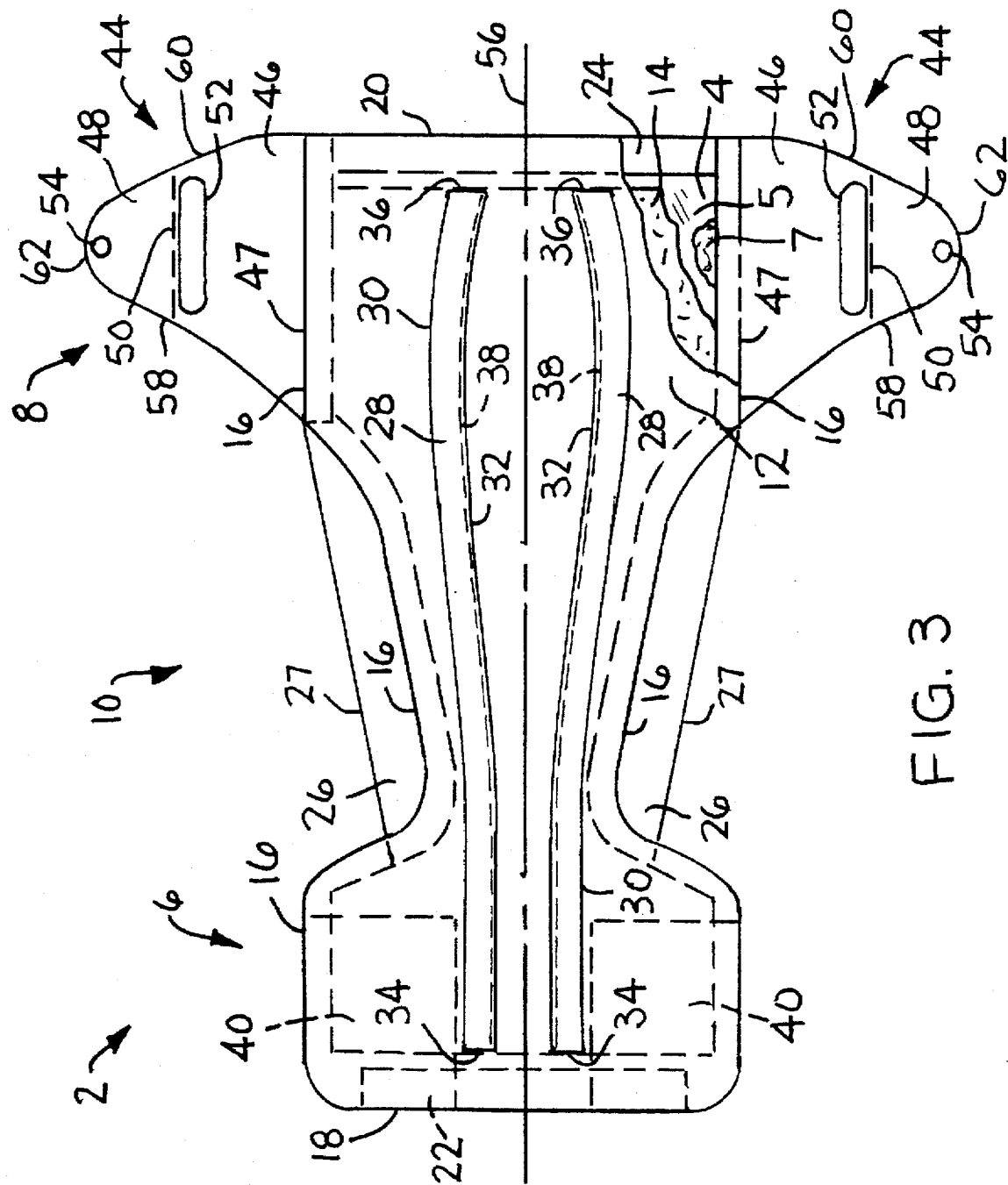
FIG. 3 is a broken-away top plan view of the embodiment in FIG. 1 laid flat.

Referring to FIG. 3, absorbent article 2 of the present invention comprises backsheet 4 including front section 6, back section 8, and crotch section 10, a topsheet 12, and absorbent medium 14 disposed between backsheet 4 and topsheet 12. Backsheet 4 has a shape generally appearing as an hourglass shape, and topsheet 12 has a similar shape. Absorbent medium 14 is smaller in size than backsheet 4 and topsheet 12 so that backsheet 4 and topsheet 12 can be joined together in any suitable manner.

Backsheet 4 further includes oppositely disposed lateral sides 16, front end 18, and back end 20. Although the present description will describe other elements as being attached or disposed with backsheet 4, the present invention contemplates that such attachments can be associated only with topsheet 12, or with both backsheet 4 and topsheet 12. For example, it may be desirable that backsheet 4 have a smaller size, which can be accomplished by making backsheet 4 shorter than topsheet 12, narrower than topsheet 12, or both shorter and narrower than topsheet 12. The portions of topsheet 12 that extend beyond the peripheral boundaries of backsheet 4 may have other elements attached thereto. Should backsheet 4 and topsheet 12 be of identical shape, then attachments of other elements can be to backsheet 4 alone, topsheet 12 alone, or both backsheet 4 and topsheet 12.

In the description that follows, front section 6, back section 8, and crotch section 10, which were described above as portions of backsheet 4, will also serve to identify those particular areas of absorbent article 2 and topsheet 12.

At front section 6, front waist elastic 22 is positioned between backsheet 4 and topsheet 12 and, in this preferred embodiment, is attached to both backsheet 4 and topsheet 12. It is preferred that front waist elastic 22 has a relaxed, attached length of about 4.5 inches and a stretched, attached length of about 6.0 inches.

Similarly, back section 8 includes back waist elastic 24 positioned between and joined to backsheet 4 and topsheet 12. Back waist elastic 24 has a preferred relaxed, attached length of about 4.5 inches, and a stretched, attached length of about 7.0 inches.

A pair of stretchable leg cuffs 26 are disposed on opposite lateral sides 16 at least in crotch section 10 of absorbent article 2. Stretchable leg cuffs 26 can be a stretch-bonded laminate (SBL) material in which the outer layers are made of a gatherable material, and the inner layer is made of a stretchable material. The laminate is formed by stretching the stretchable layer and then attaching the stretched layer to the gatherable layers. When the attached layers are then relaxed, the gatherable layers are gathered and the stretched layer returns to a relaxed, non-gathered state. When one of the gatherable layers is made of a liquid-impermeable material, then leg cuffs 26 also serve as liquid-impermeable leg cuffs. Stretchable leg cuffs 26 also can be made of a single layer of liquid-impermeable or liquid-permeable material elasticized by at least one elastic strand attached in a stretched condition to the distal or outermost edge portion 27 of each leg cuff 26. In a preferred embodiment, leg cuffs 26 comprise a layer of liquid-impermeable material and another layer of material that sandwich therebetween a plurality of strands of elastic material. The elastic strands are stretched between the layers, which are then bonded together to form a three-layered SBL material.

Preferably, stretchable leg cuffs 26 have a relaxed, attached length of about 6.25 inches, a stretched, attached length of about 8.25 inches, and an ultimate stretched length of about 11.50 inches.

Disposed on opposite sides of crotch section 10 are a pair of containment flaps 28 which are preferably made of the same material as topsheet 12. Containment flaps 28 may be formed in generally one of two ways. The first is to form each containment flap 28 from topsheet 12. The second is to make containment flaps 28 as individual elements and then attach them in any suitable manner to topsheet 12. With the latter method, each proximal edge 30 of a respective containment flap 28 is attached in any suitable manner to topsheet 12. In the former method, topsheet 12 is essentially pleated with its innermost or proximal edge 30 adhered together in any suitable manner. In both methods, distal edges 32 include at least a single strand 38 of stretchable material that is attached in a stretched condition. The front ends 34 and back ends 36 of containment flaps 28 are folded inwardly toward the center of absorbent article 2 and secured to topsheet 12. Upon relaxing or fitting absorbent article 2 to the wearer, elastic strands 38 in distal edges 32 cause edges 32 to extend upwardly from topsheet 12 as viewed in FIG. 3. As described, containment flaps 28 are located inwardly or inboard of stretchable leg cuffs 26. A more detailed description of the construction of flaps 28 is contained in U.S. Pat. No. 4,704,116 to Enloe, the contents of which are incorporated by reference herein.

Although absorbent article 2 in a preferred embodiment includes containment flaps 28, containment flaps 28 may not be necessary depending upon several factors such as, but not limited to, the types of absorbent materials of which absorbent medium 14 is made, whether or not stretchable leg cuffs 26 include a liquid-impermeable layer, cost of materials, and the like.

Figure 1:
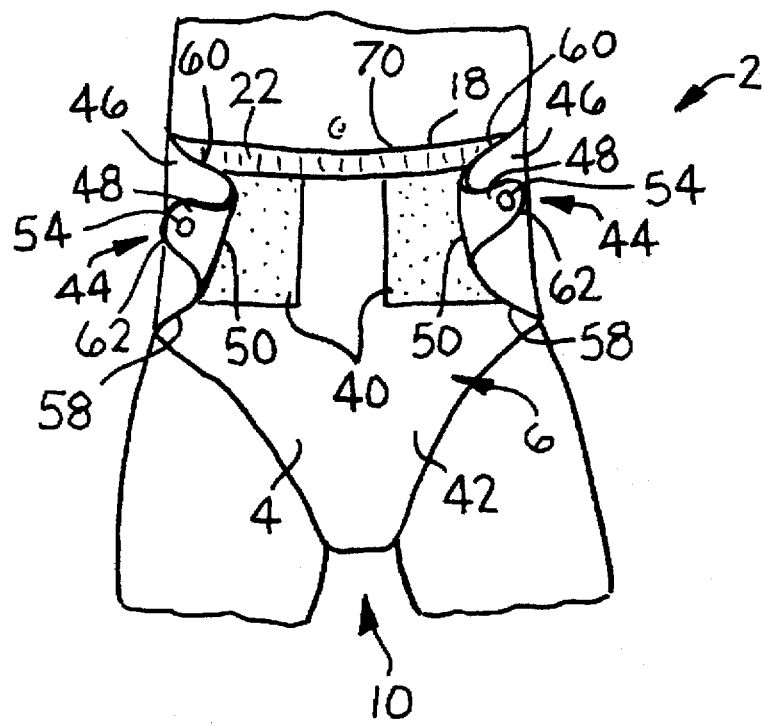
FIG. 1 is a front elevational view of a preferred embodiment of the present invention being initially fitted onto a wearer.

Referring to FIGS. 1 and 3, a pair of loop panels 40 are joined to outer surface 42 of backsheet 4. Although FIG. 1 illustrates a pair of loop panels 40, it may be a single panel extending across the front of backsheet 4. The loop material may be of any suitable material that is compatible with the hook material to be described below, and a preferred loop material can be purchased from Guilford Mills, Inc., 6001 W. Market Street, Greensboro, N.C. 27402-0004. The material is identified as Guilford Loop 18903 or 19902. Preferably, there are two loop panels 40, and each has a length, as measured in a direction parallel to a longitudinal axis of absorbent article 2, of about 3.5 inches from front end 18. The width of each loop panel 40, as measured in a direction parallel to a lateral or transverse centerline of absorbent article 2, is about 2.75 inches.

Absorbent article 2 further comprises a pair of differentially stretchable ears 44 attached to back section 8 and extending outwardly therefrom. Each stretchable ear 44 includes a stretchable inner ear portion 46 having an inner edge 47 connected to a lateral side 16 of back section 8, stretchable outer ear portion 48 extending outwardly from stretchable inner ear portion 46 at juncture 50 therebetween, hook panel 52 joined to stretchable ear 44 at juncture 50, and snap fastener 54 near the outermost portion of stretchable outer ear portion 48. Inner edge 47 has a length between about 3 inches to about 6 inches, and preferably about 5 inches. This length of inner edge 47 is important in providing a snug and secure fit of diaper 2 against the sides of the wearer. If inner edge 47 is less than about 3 inches, inner ear portion 46 tends to fold or curl at its sides 58, 60, thereby resulting in a less snug or secure fit at the wearer's sides. If inner edge 47 is greater than about 6 inches, then the bend of the wearer's front leg at the hip and crotch area may tend to buckle or curl inner ear portion 46.

Hook panel 52 is compatible with a respective loop panel 40, and preferably is a hook material that can be purchased from Velcro, U.S.A., Manchester, N.H. The material is identified as Hook HTH 708.

Figure 2:
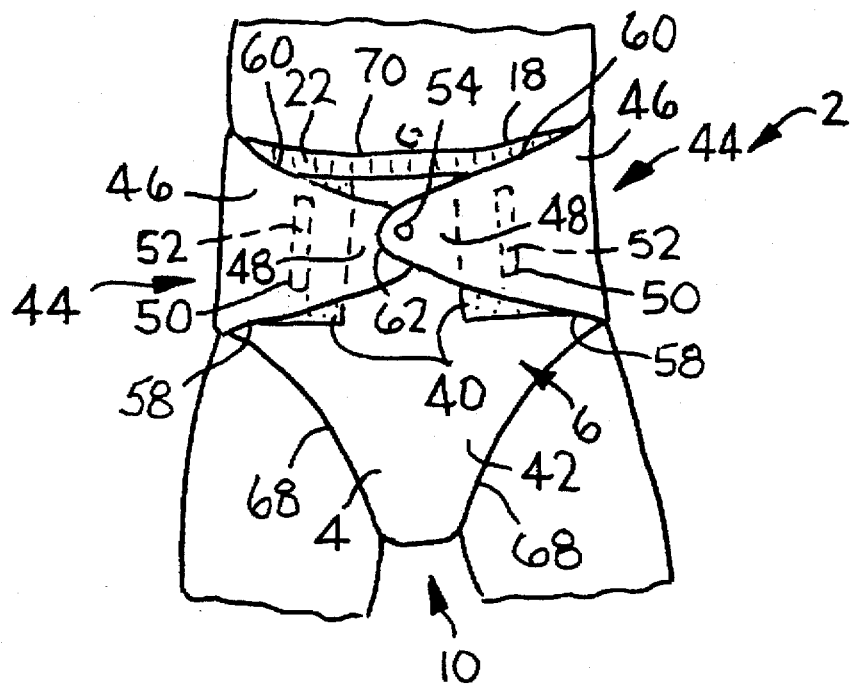
FIG. 2 is the same as FIG. 1 except that the embodiment has been completely fitted onto the wearer.

Snap fastener 54 includes a male portion on one ear 44 and the female portion on the other ear 44. Other types of mechanical fasteners can be utilized with the present invention such as, but not limited to, hook and loop fasteners, hook-and-eye fasteners, and the like. The primary purpose of snap fastener 54 is to provide a childproof fastening system to prevent the child from inadvertently or intentionally opening and removing absorbent article 2. Accordingly, snap fastener 54 should have an unfastening force or snap action in the range of about 500 to about 1500 grams force, and preferably about 1000 grams force. The unfastening force or snap action is the force required to open or unsnap snap fastener 54, and is designed to permit an adult to open snap fastener 54 while preventing the child from doing so. As illustrated in FIG. 2, stretchable ears 44 are brought together at the front of the wearer and snap fastener 54 is fastened together.

In accordance with the principles of the present invention, stretchable inner ear portions 46 and stretchable outer ear portions 48 have different stretch characteristics either when relaxed or when stretched and fastened as described hereafter. Preferably, each stretchable inner ear portion 46 has a higher tension than stretchable outer ear portions 48, and each portion 46 has an elongation that permits hook panels 52 to be easily stretched about the sides of the wearer and attached to a respective loop panel 40. The positioning and attaching of hook panels 52 to loop panels 40 is the final step in properly fitting absorbent article 2 a wearer. Because of the relatively long dimension of inner edge 47 of each stretchable ear 44 near lateral sides 16 of back section 8, stretchable ears 44 provide the primary support and fit for absorbent article 2 along the wearer's hip-waistline area.

Each stretchable outer ear portion 48 preferably has a lower tension than stretchable inner ear portions 46, and each portion 48 preferably has an elongation equal to or greater than that of a stretchable inner ear portion 46. Because stretchable inner ear portions 46 are used primarily to fit and support absorbent article 2 on the wearer, stretchable outer ear portions 48 may have a lower tension so that they easily stretch to permit snap fastener 54 to be closed without adding additional tension or stretch to inner ear portions 46 that provide the proper fit and support. With the unfastening force or snap action required to open snap fastener 54, this provides a childproof feature to absorbent article 2 without negatively affecting the proper fit and support provided by stretchable inner ear portions 46, hook panels 52, and loop panels 40. The desired snug, trim fit is provided by inner ear portions 46 having a higher tension when hook panels 52 are fastened on loop panels 40 than the tension of outer ear portions 48 when snap fastener 54 is snapped together.

The preferred range of tension for each stretchable inner ear portion 46 is between about 100 grams force to about 5,000 grams force, and preferably about 200 grams force to about 1,500 grams force. A preferred range of tension for each stretchable outer ear portion 48 is between about 100 grams force to about 5,000 grams force, and preferably about 200 grams force to about 1,500 grams force. These tension ranges are calculated as directed in American Society of Testing and Material (ASTM) Test Method D 4964-89.

The preferred range of elongation for each stretchable inner ear portion 46 is between about 20% to about 300%, and preferably about 25% to about 150%. A preferred range of elongation for each stretchable outer ear portion 48 is about 20% to about 300%, and preferably about 25% to about 150%.

The differing tensions between relaxed stretchable outer ear portions 48 and relaxed stretchable inner ear portions 46 can be provided in several ways. In FIG. 3, each inner ear portion 46 and outer ear portion 48 are made of the same stretchable material. In order to provide the differing tension ranges, each stretchable ear 44 has tapering sides 58, 60 that converge to form generally rounded end 62. Side 58 convergingly tapers in a concave manner toward end 62, and side 60 convergingly tapers in a generally convex manner toward end 62. Sides 58 have a slightly concave cut or form to provide better fit across the side hip area of the wearer. Sides 60 are slightly convex so as to provide a better fit near the waistline.

The present invention contemplates that sides 58, 60 can be straight or curved in a different manner and still be within the principles of the present invention.

In FIG. 3, the differing tension characteristics are provided by the convergingly tapering sides 58, 60 which result in each inner ear portion 46 having a greater amount of stretchable material than a respective outer ear portion 48, assuming of course a constant thickness of the stretchable material. This greater amount of stretchable material in the design of FIG. 3 results in inner ear portion 46 having a higher tension than outer ear portion 48. The degree of difference in tension ranges between outer ear portions 48 and inner ear portions 46 depend upon several factors such as the surface area of each portion, the length and width of each portion, and the relative shapes of each portion.

Figure 4:
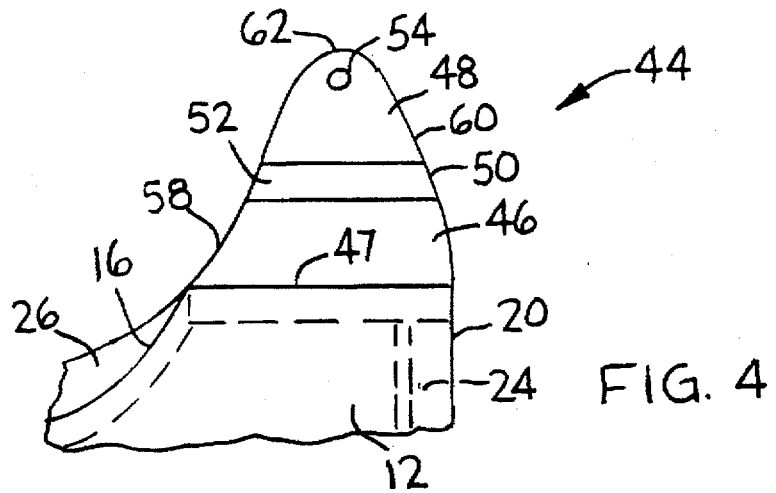
FIG. 4 is a top plan, fragmentary view of a modified ear portion.

Referring to FIG. 4, each stretchable ear 44 can be made of two stretchable materials having different stretch characteristics. For example, stretchable inner ear portion 46 can be made of a stretchable material having a specific tension range and elongation range, and stretchable outer ear portion 48 can be made of a second stretchable material having a tension range less than that of the material of stretchable inner ear portion 46 and an elongation range at least equal to or greater than that of the material of stretchable inner ear portion 46. Although FIG. 4 illustrates stretchable ear 44 as being identical in shape to stretchable ear 44 in FIG. 3, ear 44 in FIG. 4 could be of square or rectangular shape and still provide the differing stretch characteristics because of the different stretchable materials of which it is made. In FIG. 4, hook panel 52 joins ear portions 46, 48 together and can be accomplished in any suitable manner, such as by adhesive or thermal bonding.

Figure 5:
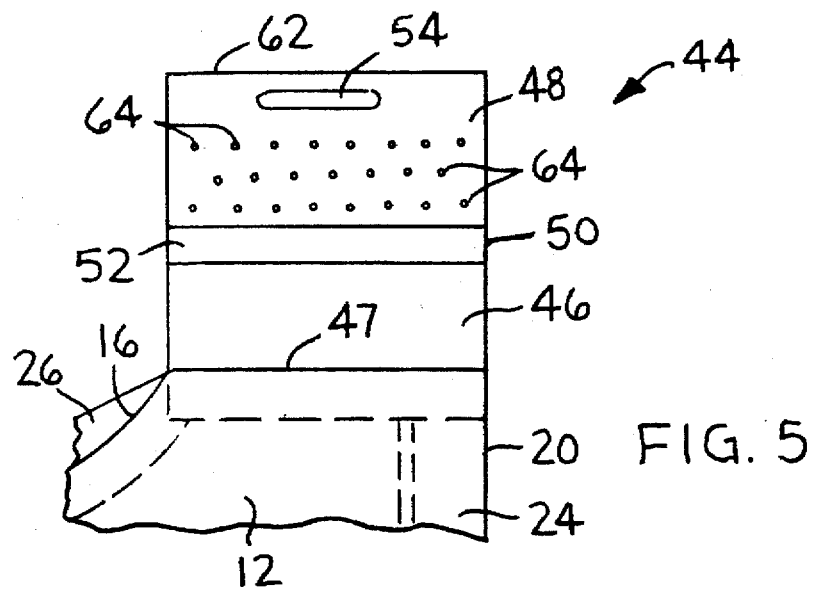
FIG. 5 is a top plan, fragmentary view of another ear portion.

FIG. 5 illustrates a generally rectangular stretchable ear 44 that can be made of the same stretchable material as ear 44 in FIG. 3 or different stretchable materials as ear 44 in FIG. 4. If stretchable outer ear portion 48 is made of the same material as stretchable inner ear portion 46, or if stretchable outer ear portion is made of a different stretchable material that has a greater tension range than stretchable inner ear portion 46, then stretchable outer ear portion 48 can be provided with a plurality of holes 64 therethrough. Since holes 64 are provided through stretchable outer ear portion 48, the tension range is lowered below the tension range of stretchable inner ear portion 46. Holes 64 serve to kill or destroy a portion of the stretch characteristics of the material. Holes 64 can be provided by needling, ultrasonics and the like. If desired and as illustrated in FIG. 5, snap fastener 54 can be of racetrack shape to accommodate the non-tapering shape of ear 44 in FIG. 5. Although illustrated as rectangular, the preferred shape of ear 44 is that shape illustrated at FIG. 3.

Figure 6:
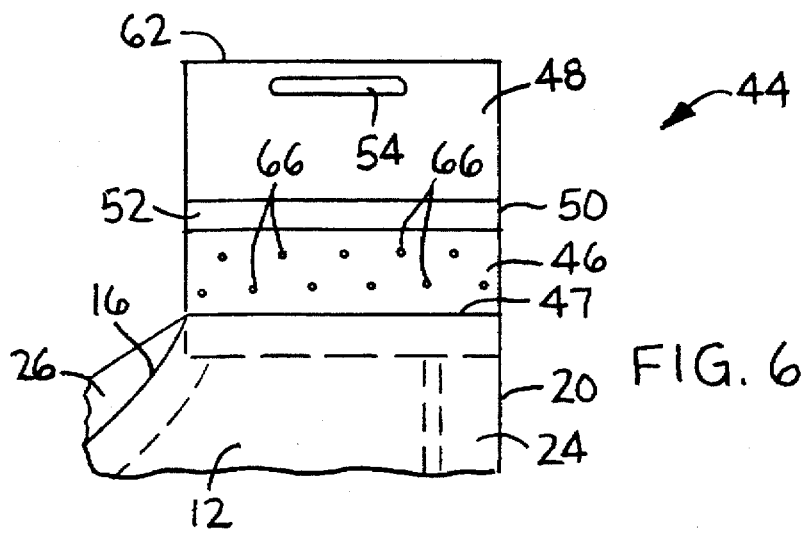
FIG. 6 is a top plan, fragmentary view of another ear portion.

FIG. 6 illustrates another stretchable ear 44 in which stretchable outer ear portions 48 and stretchable inner ear portions 46 can be made of the same or differing stretchable materials. In this embodiment in FIG. 6, stretchable inner ear portions 46 are provided with a higher tension range than stretchable outer ear portions 48 by a plurality of bond points 66 that effectively increase the tension characteristics of the original stretchable material. Bond points 66 are not apertures through the stretch material, but rather are hardened spots or surfaces in the material.

Although holes 64 in FIG. 5 and bond points 66 in FIG. 6 are illustrated as circular in shape, other shapes can be used and fall within the principles of the present invention.

Absorbent article 2 can be placed on a child as the child is lying on his or her back by positioning article 2 under the child's buttocks. One or both of stretchable ears 44 can be brought around to the front of the diaper, and during this movement of stretchable ears 44 around to front section 6, the desired fit, i.e., stretching of ears 44, is accomplished. Hook panels 52 are then attached to loop panels 40. At this time, if the caretaker or mother decides the fit is too loose or too tight, the fit can be adjusted by repositioning hook panels 52 on loop panels 40. This portion of fitting article 2 on the child is accomplished with stretchable inner ear portions 46 to obtain the desired fit. Thereafter, stretchable outer ear portions 48 are stretched across the front section 6 in order to secure snap fastener 54. Because stretchable inner ear portions 46 are relatively wide at their juncture, i.e., inner edges 47, with lateral sides 16 as seen in FIGS. 1 and 2, excellent support is provided at the hip to waist area to prevent diaper sag and droop during wear. As illustrated in FIGS. 1 and 2, stretchable inner ear portions 46 extend from the waistline down to the outer side of the hip area. Removal of the diaper is the reverse of fitting it.

Alternatively, article 2 can be closed to form a pant-like garment, which can then be fitted to the child. This can be accomplished by snapping snap fastener 54 and, if desired at this time, positioning hook panels 52 on loop panels 40 at their approximate desired positions. Thereafter, article 2 can be fitted to the child by extending the child's legs through the leg openings 68 and waist opening 70, and then pulling article 2 upwardly to the waistline as illustrated in FIGS. 1 and 2. If hook panels 52 have not been attached to loop panels 40 and only snap fastener 54 has been snapped, then once article 2 is pulled upwardly to the area of fit on the wearer, hook panels 52 can be grasped and positioned on loop panels 40 as desired. This method of fitting article 2 may aid in toilet training the child, and provides a convenient standing change when adequate diapering facilities are unavailable or the child is uncooperative.

Because snap fastener 54 is located on the outermost extremities of stretchable ears 44, i.e., stretchable outer ear portions 48, snap fastener 54 is more easily closed or snapped compared to other garments in which the female or male portion of the snap fastener is attached to front section 6 of article 2. In the latter case, the mother is required, once the diaper has been fitted, to insert her hand between the child and the front of the diaper to provide a firm basis or foundation for snapping the fastener together. Otherwise, the caretaker must push inwardly against the child's abdomen in order to fasten the fastener. In the present invention, article 2 has been properly fitted to the child once hook panels 52 are attached to loop panels 40, and because stretchable outer ear portions 48 have a lower tension, the mother or caretaker can simply grasp stretchable outer ear portions 48 and snap the snap fastener 54 together.

Although absorbent article 2 has been described as having a single snap fastener, multiple mechanical fastening devices can be used within the principles of the present invention. Similarly, the present invention contemplates other modifications to absorbent article 2 such as, but not limited to, varying the length or widths or stretch characteristics of waist elastics 22, 24, and stretchable leg cuffs 26, and elastic strands 38. Also, containment flaps 28 can be designed to be shorter in length than absorbent article 2.

The process for making absorbent article 2 includes adhering absorbent medium 14 to backsheet 4 by lines or a spray of suitable adhesive, and attaching topsheet 12 and backsheet 4 along their peripheries by lines of glue or ultrasonic bonding, heat sealing, or the like. Waist elastics 22, 24 are attached between backsheet 4 and topsheet 12, or attached to the outermost side of backsheet 4 or the innermost side of topsheet 12. Waist elastics 22, 24 can be attached in a stretched condition or, if made of a heat-elasticizable material, are attached in a relaxed condition and then heated to cause them to gather elastically. Stretchable leg cuffs 26 are attached between backsheet 4 and topsheet 12, and can be attached to either backsheet 4 or topsheet 12 or to both of them. The attachment is accomplished so as not to gather the layer or material to which they are attached. For example, if leg cuffs 26 are to be attached only to backsheet 4, cuffs 26 can be attached while in a relaxed condition to backsheet 4, or can be slightly pleated and then attached to backsheet 4. In either method, backsheet 4 is non-gathered as compared to prior art diapers in which the leg elastics are attached while in a stretched condition. Loop panels 40 and hook panels 52 can be adhered to backsheet 4 and stretchable ears 44, respectively, with lines or spray of adhesive or other bonding techniques. Stretchable ears 44 can be similarly secured to lateral sides 16 of absorbent article 2. Snap fastener 54 is attached in the manner conventional for the type of fastener being used.

Backsheet 4 is preferably provided with a cloth-like feel on its outermost side, i.e., the side opposite the baby's skin. One method of accomplishing this is to make backsheet 4 as a two-layer composite. Preferably, backsheet 4 is a two-layer laminate comprising an inner liquid-impermeable layer 5 (FIG. 3) of polypropylene film having a thickness of about 0.6 mil, and an outer cloth-like layer 7 of spunbond polypropylene having a basis weight of about 0.7 ounces per square yard. The spunbond polypropylene layer 7 preferably is a bilobal fiber having a denier of about 2.0 with a wire weave bond pattern. The inner and outer layers 5, 7 can be joined in any suitable manner, such as by spray adhesive, lines of adhesive, dot bonding, extruding layer 5 onto layer 7, and the like. Backsheet 4 may be made of other materials that are suitably liquid-impermeable or treated to be so. Examples are meltblown or film material made of polyethylene or polyolefin copolymers. Backsheet 4 may also be vapor permeable as well as liquid impermeable, if desired.

Topsheet 12 can be a liquid permeable, hydrophilic or hydrophobic material, such as a spunbond web of synthetic polymer filaments; a spun lace web; a spunbond-meltblown web; or the like. Suitable synthetic polymers include polyethylene, polypropylene, polyester, and nylon. Topsheet 12 also can be a Kraton meltblown/polypropylene spunbond stretch-bonded laminate which has been apertured and made wettable by addition of suitable surfactants. Topsheet 12 can be made stretchable by use of heat-shrinkable fibers or elastic fibers that are first stretched and then attached to the spunbonded layer.

Unique to the present invention is the increased softness provided to topsheet 12 by use of bicomponent fibers. Topsheet 12 is an integrated two-layer bonded-carded-web having a basis weight of about 1.5 ounces per square yard. One of the layers is preferably a polyethylene/polyester bicomponent fiber having a denier of about 2.25 and a basis weight of about 0.5 ounce per square yard. The core of this fiber is polyester having a sheath of polyethylene surrounding it. This type of bicomponent fiber can be purchased from BASF Corporation, Fibers Division, Enka, N.C. 28728. The other layer has a basis weight of about 1.0 ounce per square yard and comprises 75 percent by weight of polyester fiber having a thickness of about 15 denier per fiber, and 25 percent by weight of a polyethylene/polypropylene bicomponent fiber, which can be purchased from CHISSO Corp., PP Fiber Division, 6-32, Nakanoshima 3, Kita-Ku, Osaka-530, Japan. These two layers can be integrated together by, for example, through-air or infra-red bonding. Topsheet 12 preferably has a density of about 0.02 grams per cubic centimeter and a bulk thickness of about 0.10 inches. Besides being a sheath-core design, the bicomponent fibers may also be side-by-side.

Although the above is a preferred embodiment of topsheet 12, topsheet 12 can have a basis weight between about 15 to about 102 gsm (grams per square meter), a density between about 0.01 to about 0.08 gcc (grams per cubic centimeter), a fiber denier between about 1 to about 15, fiber lengths between about 0.5 to about 2.0 inches, and in which the fibers may be crimped in a range of about 14 to about 22 crimps per inch.

Containment flaps 28 can be made of the same material as topsheet 12, and can be integrally formed therefrom or can comprise separate structure joined to topsheet 12 in any suitable manner, such as by one or more lines of adhesive.

Stretchable leg cuffs 26 may also be made of any suitable material having elastic or stretchable properties. Examples of such materials include films or layers of natural rubber, synthetic rubber, or thermoplastic elastomeric polymers, and can be panels, or single or multiple threads or filaments or ribbons thereof. These materials may also be heat-shrinkable or heat-elasticizable. Furthermore, these stretchable materials may be formed with gatherable layers, such as spun-bonded polymer materials, as a stretch-bonded laminate. For example, a suitable stretch-bonded laminate comprises two gatherable layers of 0.4 ounce per square yard of spunbond polypropylene having therebetween a layer of meltblown elastic material such as a Kraton elastic in either layer form or separate threads of material having a basis weight of about 0.5 ounce per square yard. The layer of the elastomeric is stretched, the two layers of polypropylene then joined to the elastomeric layer, and upon relaxing the layers, the polypropylene layers gather. Leg cuffs 26 can be breathable or non-breathable.

Waist elastics 22, 24, elastic strands 38, and stretchable ears 44 can be made of the same materials as leg cuffs 26 or other similar materials.

Absorbent medium 14 can be made of any suitable absorbent material or materials such as cellulosic fibers, synthetic fibers, absorbent gelling materials in the form of particles, fibers, layers and the like, and various mixtures or blends thereof. Suitable absorbent gelling materials can be in organic materials such as silica gels or organic compounds such as cross-linked polymers. Absorbent medium 14 can also be wrapped in a tissue wrap in order to maintain the integrity of absorbent medium 14.

Although the above preferred embodiment has been described with each inner ear portion 46 having a higher tension than each outer ear portion 48 when the ears are relaxed, and each outer ear portion 48 having an elongation at least equal to or greater than each inner ear portion 46 when the ears are relaxed, the present invention contemplates each inner ear portion 46 having a lesser or equal tension and elongation than each outer ear portion 48. Thus, in order to have a higher tension at inner ear portions 46, this means that inner ear portions 46 would be stretched and applied with a tension greater than the stretched and applied tension of outer ear portions 48, thereby resulting in ears 44 being differentially stretchable. The word "applied" here meaning the stretched, fastened condition of each ear portion when the diaper has been fitted on the wearer.

While this invention has been described as having preferred embodiments, it will be understood that it is capable of further modifications. This application is therefore intended to cover any variations, equivalents, uses, or adaptations of the invention following the general principles thereof, and including such departures from the present disclosure as come within known or customary practice in the art to which this invention pertains and falls within the limits of the appended claims.

What is claimed is:

1. An absorbent article, comprising:
   a front section, a back section having oppositely disposed side portions, and a crotch section,
   an absorbent medium disposed on at least said crotch section, and
   a pair of differentially stretchable ears being disposed on respective oppositely disposed side portions of said back section,
   each said differentially stretchable ear comprising a stretchable inner ear portion having a first stretchable characteristic and a stretchable outer ear portion having a second stretchable characteristic, said inner and outer ear portions having differing tension characteristics when relaxed.

2. The article of claim 1 wherein said outer ear portions have a lower tension than said inner ear portions when in use.

3. The article of claim 1 wherein said outer ear portions have a higher tension than said inner ear portions when in use.

4. The article of claim 1 wherein said outer ear portions have a tension equal to the tension of said inner ear portions when in use.

5. The article of claim 1 wherein said outer ear portions have a higher elongation than said inner ear portions when in use.

6. The article of claim 1 wherein said outer ear portions have a lower elongation than said inner ear portions when in use.

7. The article of claim 1 wherein said outer ear portions have an elongation equal to an elongation of said inner ear portions when in use.

8. The article of claim 1 wherein said inner and said outer ear portions are made of the same stretchable material, said outer ear portions having a plurality of holes therethrough.

9. The article of claim 1 wherein said inner and said outer ear portions are made of a stretchable material, said inner ear portions having a plurality of bond points thereon.

10. The article of claim 1 wherein said inner and said outer ear portions are made of different stretchable materials.

11. The article of claim 1 wherein said inner and said outer ear portions are made of a stretchable material.

12. The article of claim 1 wherein each said inner ear portion is joined to a respective said side portion of said back section along a length of said side portion of said back section of from about 3 to about 6 inches.

13. The article of claim 1 further comprising a topsheet comprising bicomponent fibers.

14. The article of claim 13 wherein said bicomponent fibers are sheath-core fibers.

15. The article of claim 13 wherein said bicomponent fibers are side-by-side fibers.

16. The article of claim 13 wherein said topsheet has a basis weight between about 15 to about 102 grams per square meter and a density between about 0.01 to about 0.08 grams per cubic centimeter.

17. The article of claim 13 wherein said fibers have a thickness between about 1 to about 15 denier per fiber, and a length between about 0.5 to about 2.0 inches.

18. The article of claim 13 wherein said fibers have a crimp between about 14 to about 22 crimps per inch.

19. The article of claim 1 further comprising a first engaging member on each said ear and a second engaging member on said front section, said first and said second engaging members being releasably engageable together.

20. The article of claim 19 wherein each said first engaging member is disposed near a respective juncture of said inner and said outer ear portions.

21. The article of claim 20 wherein each said first engaging member is a plurality of hook members and said second engaging member is a plurality of loop members.

22. The article of claim 19 further comprising a first fastening member on one of said outer ear portions, and a second fastening member on the other of said outer ear portions, said first and said second fastening members being releasably fastenable together.

23. The article of claim 22 wherein said first and said second fastening members have a snap action between about 500 to about 1500 grams-force.

24. An absorbent article, comprising:
a front section, a back section having oppositely disposed side portions and a crotch section having oppositely disposed lateral sides,
an absorbent medium being disposed on said crotch section,
a pair of stretchable ears being disposed on respective generally oppositely disposed side portions of said back section, each said stretchable ear comprising a stretchable inner ear portion and a stretchable outer ear portion,
a first engaging member on each said ear, and a second engaging member on said front section, said first and said second engaging members being releasably engageable together, and
a first fastening member on one of said outer ear portions and a second fastening member on the other of said outer ear portions, said first and said second fastening members being releasably fastenable together while said first engaging member on each said ear is engaged with said second engaging member.

25. The article of claim 24 wherein said outer ear portions have a lower tension characteristic than said inner ear portions when relaxed.

26. The article of claim 24 wherein said outer ear portions have a higher tension characteristic than said inner ear portions when relaxed.

27. The article of claim 24 wherein said outer ear portions have a tension characteristic equal to a tension characteristic of said inner ear portions when relaxed.

28. The article of claim 24 wherein said outer ear portions have a higher elongation than said inner ear portions when in use.

29. The article of claim 24 wherein said outer ear portions have a lower elongation than said inner ear portions when in use.

30. The article of claim 24 wherein said outer ear portions have an elongation equal to an elongation of said inner ear portions when in use.

31. The article of claim 24 wherein said first and said second fastening members have a snap action between about 500 to about 1500 grams.

32. The article of claim 24 wherein said inner and said outer ear portions are made of a stretchable material, said outer ear portions having a plurality of holes therethrough.

33. The article of claim 24 wherein said inner and said outer ear portions are made of a stretchable material, said inner ear portions having a plurality of bond points thereon.

34. The article of claim 24 wherein said inner and said outer ear portions are made of different stretchable materials.

35. The article of claim 24 wherein said inner and said outer ear portions are made of a stretchable material.

36. The article of claim 24 wherein said stretchable ears are joined to said side portions along a length of said side portion of said back section of from about 3 to about 6 inches.

37. The article of claim 24 further comprising a topsheet comprising bicomponent fibers.

38. The article of claim 37 wherein said bicomponent fibers are sheath-core fibers.

39. The article of claim 37 wherein said bicomponent fibers are side-by-side fibers.

40. The article of claim 37 wherein said topsheet has a basis weight between about 15 to about 102 grams per square meter and a density between about 0.01 to about 0.08 grams per cubic centimeter.

41. The article of claim 37 wherein said fibers have a thickness between about 1 to about 15 denier per fiber, and a length between about 0.5 to about 2.0 inches.

42. The article of claim 37 wherein said fibers have a crimp between about 14 to about 22 crimps per inch.

43. The article of claim 24 further comprising a pair of containment flaps being disposed at said respective generally oppositely disposed lateral sides of said crotch section.

44. The article of claim 43 wherein said containment flaps are liquid permeable.

45. The article of claim 24 further comprising a pair of leg cuffs being disposed at said respective generally oppositely disposed lateral sides of said crotch section.

46. The article of claim 45 further comprising a pair of containment flaps being disposed inwardly of said leg cuffs.

47. The article of claim 46 wherein said containment flaps are liquid permeable.

48. The article of claim 47 wherein said leg cuffs are liquid impermeable.

49. An absorbent article, comprising:
a front section, a back section having oppositely disposed side sections, and a crotch section having oppositely disposed lateral sides,
an absorbent medium disposed at least at said crotch section,
a pair of stretchable ears being disposed on respective oppositely disposed side portions of said back section, each said stretchable ear comprising a stretchable inner ear portion having a first stretchable characteristic and a stretchable outer ear portion having a second stretchable characteristic,
a stretchable leg cuff attached at each said lateral side of said crotch section,
said stretchable leg cuffs being attached so as not to gather a material to which they are attached when said leg cuffs are relaxed, and
a pair of containment flaps disposed on said opposite sides of said crotch section.

50. The article of claim 49 further comprising a first engaging member on each said ear and a second engaging member on said front section, said first and said second engaging members being releasably engageable together.

51. The article of claim 50 wherein each said first engaging member is a plurality of hook members and said second engaging member is a plurality of loop members.

52. The article of claim 50 further comprising a first fastening member on one of said outer ear portions, and a second fastening member on the other of said outer ear portions, said first and said second fastening members being releasably fastenable together.

53. The article of claim 49 further comprising a topsheet comprising bicomponent fibers.

54. The article of claim 53 wherein said bicomponent fibers are sheath-core fibers.

55. The article of claim 53 wherein said topsheet has a basis weight between about 15 to about 102 grams per square meter and a density between about 0.01 to about 0.08 grams per cubic centimeter.

56. The article of claim 55 wherein said fibers have a thickness between about 1 to about 15 denier per fiber, and a length between about 0.5 to about 2.0 inches.

57. The article of claim 53 wherein said fibers have a crimp between about 14 to about 22 crimps per inch.

58. The article of claim 53 wherein said bicomponent fibers are side-by-side fibers.

* * * * *